(12) United States Patent
Franck

(10) Patent No.: US 12,025,600 B2
(45) Date of Patent: Jul. 2, 2024

(54) METHOD FOR THE RADIOLOGICAL CHARACTERISATION OF THE RADIATION LISTING OF MERCURY

(71) Applicant: ARGENTUM VIVUM SOLUTIONS, Hamburg (DE)

(72) Inventor: Michael Franck, Lubeck (DE)

(73) Assignee: ARGENTUM VIVUM SOLUTIONS, Hamburg (DE)

( * ) Notice: Subject to any disclaimer, the term of this patent is extended or adjusted under 35 U.S.C. 154(b) by 414 days.

(21) Appl. No.: 17/287,332

(22) PCT Filed: Jun. 8, 2020

(86) PCT No.: PCT/DE2020/100480
§ 371 (c)(1),
(2) Date: Apr. 21, 2021

(87) PCT Pub. No.: WO2020/249159
PCT Pub. Date: Dec. 17, 2020

(65) Prior Publication Data
US 2021/0356449 A1    Nov. 18, 2021

(30) Foreign Application Priority Data

Jun. 11, 2019 (DE) ................ 10 2019 115 733.1

(51) Int. Cl.
*G01N 33/00* (2006.01)
*G21F 9/02* (2006.01)
*G21F 9/08* (2006.01)

(52) U.S. Cl.
CPC ..... *G01N 33/0055* (2013.01); *G01N 33/0045* (2013.01); *G21F 9/02* (2013.01); *G21F 9/08* (2013.01)

(58) Field of Classification Search
CPC ........... G01N 33/0045; G01N 33/0055; G01N 23/085; G01N 23/2204; G01N 23/2076;
(Continued)

(56) References Cited

U.S. PATENT DOCUMENTS 2,524,839 A * 10/1950 Schulman ................ G21K 4/00
430/494
2,692,948 A * 10/1954 Lion ..................... G01T 1/2935
313/538
(Continued)

FOREIGN PATENT DOCUMENTS

WO        2006/074960        7/2006

OTHER PUBLICATIONS

Bartels-Rausch et al., "Interaction of gaseous elemental mercury with snow surfaces: laboratory Â investigation; Interaction of gaseous elemental mercury with snow surfaces: laboratory investigation", *Environmental Research Letters, Environmental Research Letters, BR*, vol. 3, No. 4, pp. 45009, Oct. 2008.
(Continued)

*Primary Examiner* — Irakli Kiknadze
(74) *Attorney, Agent, or Firm* — Diederiks & Whitelaw, PLC.

(57) ABSTRACT

Mercury that may be contaminated radioactively is converted with radionuclides of other elements to a gaseous state of aggregation, which increases the distance between the mercury atoms and reduces the shielding effect of the mercury with respect to the radionuclides of other elements contained in the mercury. The method disclosed, enables the radiological characterisation of the radiation listing of mercury, without prior processing, in particular homogenization, of the sample being necessary. In particular, the method enables continuous measurement of the entire mass to be characterized and includes preparing a predefined quantity
(Continued)

of mercury, evaporating at least one fraction of the prepared mercury, and measuring the radioactive γ-radiation emitted by the gaseous mercury.

20 Claims, 1 Drawing Sheet

(58) Field of Classification Search
CPC ........... G01N 15/1459; G01N 15/1434; G01N 15/0205; G01N 2015/1006; G01N 2015/0065; G01N 2015/149; G01N 2015/1493; G01N 21/53; G01N 33/1893; G01N 15/147; G01N 2015/0088; G01N 2015/1497; G01N 2015/1486; G01N 2015/1477; G01N 15/1463; G01N 2015/0238; G21F 9/08; G21F 9/02; G21F 9/00; G21F 9/30; G21F 7/005; G21F 7/067; G01T 1/167; G01T 7/02; G01T 1/20; G01T 1/203; G01T 7/08; G01T 1/169; G01T 7/00; G01T 1/24; G01T 1/00; G01T 3/001; G01T 1/36; G01T 1/161; G01T 1/2019; G01T 1/20183; G01T 1/2018; G01T 1/003; G01T 1/202; G01T 1/208; G01T 1/178; G21D 1/003; H01L 31/18; H01L 31/085; H01L 31/032; H01J 2237/2445; B01D 29/00; A61B 5/02755; A61B 6/4258; A61B 5/6805; A61B 5/0022; H01M 14/005; H01M 8/06; G16H 40/67; H04Q 9/02; G08B 21/0453; G08B 25/016
USPC .......................................................... 378/82
See application file for complete search history.

(56) References Cited

U.S. PATENT DOCUMENTS

| | | | | |
|---|---|---|---|---|
| 3,234,388 | A * | 2/1966 | Schultz | G01K 1/00 374/188 |
| 4,966,763 | A * | 10/1990 | Skinner | C01G 13/04 423/107 |
| 6,992,580 | B2 * | 1/2006 | Kotzin | A61B 5/0022 340/539.11 |
| 2016/0370302 | A1 * | 12/2016 | Briden | G01T 3/001 |
| 2017/0160409 | A1 | 8/2017 | Furuta et al. | |
| 2020/0003913 | A1 * | 1/2020 | Kanatzidis | G01T 1/24 |

OTHER PUBLICATIONS

Klaß et al., "Measurement Concept for a Possible Clearance of Mercury Waste from Nuclear Facilities", WM2019 Conference, Mar. 2019, http://juser.fz-juelich.de/record/866956/files/Main%20document.pdf.

* cited by examiner

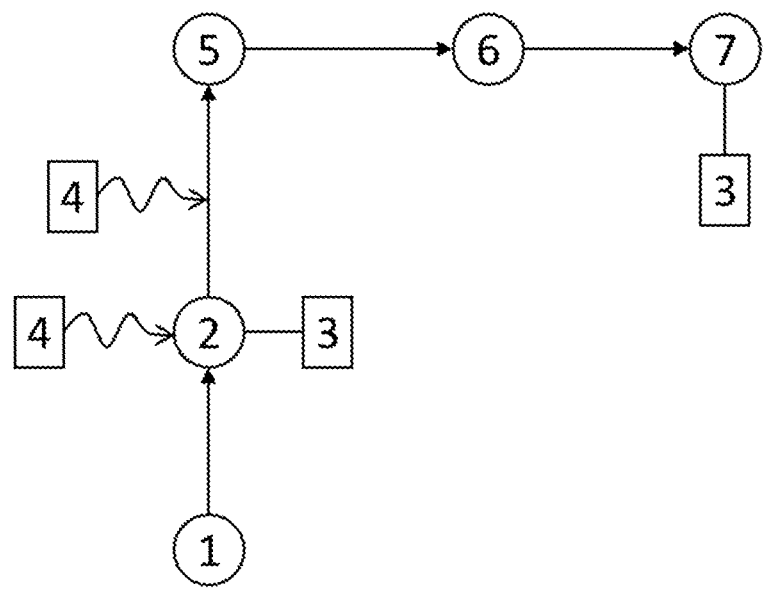

METHOD FOR THE RADIOLOGICAL CHARACTERISATION OF THE RADIATION LISTING OF MERCURY

CROSS-REFERENCE TO RELATED APPLICATIONS

This application represents the U.S. National Phase of International Application number PCT/DE2020/100480 entitled "Method for the Radiological Characterisation of the Radiation Listing of Mercury" filed 8 Jun. 2020, which claims priority to German Patent Application Number 10 2019 115 733.1 filed 11 Jun. 2019, all of which are incorporated herein by reference.

BACKGROUND OF THE INVENTION

The invention relates to a method for the radiological characterization of the radiation inventory of mercury. The invention also relates to a device for carrying out the method.

Mercury, for example from use as a sealing material in so-called hot cells, that is, heavily shielded spaces for handling and short-term storage of highly radioactive substances, or from use as a spallation target in accelerator systems, which can be contaminated with radioactive substances, must be characterized radiologically in the course of a decontamination and/or release procedure.

To quantify the radionuclides (of other elements) contained in the mercury, gamma-spectrometric measurements on individual samples are usually used to characterize the total mass, wherein radionuclides that are undetectable in this manner are additionally quantified using destructive analytical methods and taken into account for deriving suitable nuclide vectors.

This procedure is problematic in that the examined sample must be representative in order to be able to use the sample to draw conclusions about the total amount to be assessed. However, a standardized homogenization method with reproducible results for sampling mercury is not known.

Furthermore, the radiological characterization of mercury with regard to the radiation inventory has the problem that the measurement of radioactive radiation is disturbed by the mercury's high level of shielding.

SUMMARY OF THE INVENTION

The object of the invention is therefore to create a method that enables a normative radiological characterization of mercury. In particular, the object of the invention is to enable a method for checking the contamination of mercury with radionuclides, in particular of radionuclides from other non-mercury elements, in order to be able to initiate suitable decontamination and/or release procedures with regard to the radiation inventory.

According to the invention, this object is achieved by providing a predetermined amount of mercury, vaporizing at least a portion of the mercury provided to produce gaseous mercury, and detecting radioactive γ-radiation emitted by the gaseous mercury. Preferably a device for radiological characterization of radiation inventory of mercury is employed. The device includes a storage container for receiving a mercury sample to be examined. A heating device acts on the storage container for evaporating the mercury sample to produce gaseous mercury. A measuring section which is connected to the storage container has a gamma spectrometer for detecting the radioactive γ-radiation emanating from the gaseous mercury. A collecting container is connected to the measuring section for collecting the mercury sample which has passed through the measuring section.

The basic idea of the invention is to convert mercury that may be contaminated radioactively with radionuclides of other elements to the gaseous state of aggregation, which increases the distance between the mercury atoms and reduces the shielding effect of the mercury with respect to the radionuclides of other elements contained in the mercury. This procedure enables standardized radiological characterization of mercury, provided that correspondingly predetermined parameters, in particular pressure and temperature, are adhered to, without prior processing, in particular homogenization, of the sample being necessary. In particular, the method enables continuous measurement of the entire mass to be characterized.

If especially the total amount of mercury used, for example, as a sealing material for hot cells or from its use as a spallation target, is continuously measured with regard to its radiation inventory, a fractionation of the mercury with regard to the radioactivity measured in the corresponding fraction is provided. As a result of this measure, if there is increased radioactivity, it is not necessary to dispose of the total amount according to specifications, but only the fraction correspondingly contaminated with a high level of radioactivity.

In contrast to the known methods, the invention enables a qualitatively and quantitatively reliable characterization of the mercury.

In contrast to the method known from US 2017/0160409 A1, for example, that only improves the measurement of a homogeneous sample of a 0-emitter by bringing the sample converted into the gaseous state into direct contact with a large number of scintillation bodies, the present method eliminates the shielding influence of the mercury on the inventory of γ-emitters contained therein, without the need for complex sample processing.

According to the invention, therefore, a method for radiological characterization of the radiation inventory of mercury is proposed with the steps: a. Providing a predetermined amount of mercury, b. Vaporizing at least a portion of the mercury provided, and c. Detecting the radioactive γ-radiation emitted by the gaseous mercury. The mercury provided is, in particular, sealing material from hot cells or mercury from use as a spallation target.

The further steps d. Condensing the gaseous mercury, e. Collecting the condensed mercury, and f. Disposing of the mercury as a function of the measured radioactive γ-radiation, are provided, wherein the disposal can include the processing of the mercury and takes place in accordance with the prevailing regulations.

One further preferred embodiment provides that the provided amount of mercury and/or the partial amount of the provided mercury provided for evaporation and/or the collected condensed mercury are weighed, wherein the specific activity is particularly preferably determined based on the calculation of the measured radioactive γ-radiation with respect to the weight of the amount of mercury provided and/or of the provided partial amount of the mercury provided and/or of the condensed mercury collected for the evaporation.

The method specifically comprises the detection of radioactive γ-radiation by measuring the radioactive radiation using gamma spectroscopy and recording a radioactive radiation spectrum. This procedure particularly preferably enables the determination of the radionuclides contained in the mercury by means of the recorded gamma spectrum and their quantitative determination by means of gamma spectrometric methods. The mercury can thus be disposed of in a particularly preferred manner as a function of the measured radioactive γ-radiation and the type of determined radionuclides contained in the mercury.

Likewise, according to the invention, a device for the radiological characterization of the radiation inventory of mercury is proposed which has a storage container for receiving a mercury sample to be examined, a heating device acting on the storage container for evaporating the mercury sample, a measuring section connected to the storage container and having a gamma spectrometer for detecting the γ-radiation emanating from the gaseous mercury, and a collecting container connected to the measuring section for collecting the mercury sample passed through the measuring section.

A further heating device acting on the measuring section is preferably provided and keeps the mercury from the storage container in the measuring section, for example a pipeline, in the gaseous state.

Furthermore, it is preferably provided that a cooling device for condensing the gaseous mercury is set up between the measuring section and the collecting container so that the sample can be converted to its original state.

Furthermore, a first scale is preferably provided for determining the mass of the mercury sample disposed in the storage container and/or a second scale is provided for determining the mass of the mercury sample disposed in the collecting container. On the one hand, the scales can be used to determine the specific radioactivity of the mercury sample. On the other hand, the quality of the measurement and the safety of the device can be checked by comparing the values of the scales.

Finally, for safety reasons, the device is preferably designed to be vacuum- and pressure-tight.

BRIEF DESCRIPTION OF THE DRAWING

FIG. 1 shows the schematic structure of a particularly preferred exemplary embodiment of a vacuum-tight and pressure-tight device.

DETAILED DESCRIPTION OF THE PREFERRED EMBODIMENTS

The invention is explained in more detail below with reference to a particularly preferred exemplary embodiment shown in the accompanying drawing:

FIG. 1 shows the schematic structure of a particularly preferred exemplary embodiment of a vacuum-tight and pressure-tight device for the radiological characterization of the radiation inventory of mercury. The device has a storage container 1 from which the mercury sample to be examined is transferred to a storage container 2. The storage container 2 is designed to receive the mercury sample to be examined and is equipped with a heating device 4 which acts on the storage container 2 for evaporating the mercury sample.

Following the storage container 2 is a measuring section 5 that is connected to the storage container 2 and that has a gamma spectrometer for detecting the radioactive γ-radiation emanating from the gaseous mercury. The measuring section 5 is in turn connected to a cooling device 6 in which the gaseous mercury is condensed and transferred to the collecting device 7.

In addition to the heating device 4 acting on the storage container 2, a further heating device 4 acting on the measuring section 5 is provided and prevents the mercury sample from condensing in the measuring section 5.

Finally, a first scale 3 for determining the mass of the mercury sample disposed in the storage container 2 and a second scale 3 for determining the mass of the mercury sample disposed in the collecting container 7 are provided.

The device is preferably used such that, after the storage container 2 has been filled and closed, the heaters 4 are switched on. In particular, the heating device 3 acting on the measuring section is switched on first until the required operating temperature is reached; only then is the heater 4 acting on the storage container 2 switched on. A vacuum is advantageously applied.

After reaching the boiling point, the mercury sample evaporates and the mercury vapor flows from the storage container 2 through the heated measuring section 5 into the cooling device 6, in which the mercury vapor condenses. From there the mercury travels into the collecting container 7 and can be removed after the end of the measurement and sent for disposal or processing.

LIST OF REFERENCE SYMBOLS

1 Storage container
2 Storage container
3 Scale
4 Heating device
5 Measuring section
6 Cooling device
7 Collecting container

The invention claimed is:

1. A method for radiological characterization of a radiation inventory of mercury, comprising:
   a. Providing a predetermined amount of mercury having radionuclides,
   b. Vaporizing at least a portion of the mercury provided to produce gaseous mercury, and,
   c. Detecting radioactive γ-radiation emitted by the gaseous mercury.

2. The method according to claim 1, further comprising:
   d. Condensing the gaseous mercury to form condensed mercury,
   e. Collecting the condensed mercury, and,
   f. Disposing of the condensed mercury as a function of the radioactive γ-radiation.

3. The method according to claim 2, further comprising weighing the amount of mercury provided and/or the condensed mercury intended for evaporation.

4. The method according to claim 3, further comprising calculating the radioactive γ-radiation based on the weight of the amount of mercury provided and/or the condensed mercury collected for evaporation.

5. The method according to claim 2, further comprising weighing the amount of mercury provided and/or the condensed mercury intended for evaporation.

6. The method according to claim 5, further comprising calculating the radioactive γ-radiation based on the weight of the amount of mercury provided and/or the condensed mercury collected for evaporation.

7. The method according to claim 2 wherein detecting the radioactive γ-radiation includes gamma spectroscopic measurement of the radioactive radiation.

8. The method according to claim 2, further comprising determining the radionuclides contained in the mercury by a recorded gamma spectrum.

9. The method according to claim 8, wherein the mercury is disposed of as a function of the radioactive γ-radiation and a specific type of radionuclides contained in the mercury.

10. The method according to claim 1, wherein detecting the radioactive γ-radiation includes a gamma spectroscopic measurement of the radioactive radiation.

11. The method according to claim 1, further comprising determining radionuclides contained in the mercury by a recorded gamma spectrum.

12. The method according to claim 11, wherein the mercury is disposed of as a function of the radioactive γ-radiation and a specific type of radionuclides contained in the mercury.

13. A device for radiological characterization of radiation inventory of mercury comprising:
- a storage container for receiving a mercury sample to be examined,
- a heating device acting on the storage container for evaporating the mercury sample to produce gaseous mercury,
- a measuring section, which is connected to the storage container, having a gamma spectrometer for detecting radioactive γ-radiation emanating from the gaseous mercury, and,
- a collecting container connected to the measuring section for collecting the mercury sample which has passed through the measuring section.

14. The device according to claim 13, further comprising a further heating device acting on the measuring section.

15. The device according to claim 14, further comprising a cooling device arranged between the measuring section and the collecting container for condensing the gaseous mercury.

16. The device according to claim 14, further comprising a first scale for determining the mass of the mercury sample in the storage container and/or a second scale for determining the mass of the mercury sample in the collecting container.

17. The device according to claim 14, wherein the device is designed to be vacuum-tight and pressure-tight.

18. The device according to claim 13, further comprising a cooling device arranged between the measuring section and the collecting container for condensing the gaseous mercury.

19. The device according to claim 13, further comprising a first scale for determining a mass of the mercury sample in the storage container and/or a second scale for determining a mass of the mercury sample in the collecting container.

20. The device according to claim 13, wherein the device is designed to be vacuum-tight and pressure-tight.

* * * * *